United States Patent [19]

Banko

[11] 4,370,131
[45] Jan. 25, 1983

[54] ULTRASONIC TRANSDUCER TIPS

[75] Inventor: Anton Banko, Bronx, N.Y.

[73] Assignee: Surgical Design, Long Island City, N.Y.

[21] Appl. No.: 809,543

[22] Filed: Jun. 24, 1977

[51] Int. Cl.³ .............................................. A61C 1/07
[52] U.S. Cl. ...................................... 433/86; 433/119
[58] Field of Search .................... 32/58, DIG. 4, 28; 51/59 SS; 72/367; 433/86, 119

[56] References Cited

U.S. PATENT DOCUMENTS

| | | | |
|---|---|---|---|
| 1,039,728 | 10/1912 | Gilmore | 32/28 |
| 2,668,529 | 2/1954 | Hüter | 32/DIG. 4 |
| 2,831,523 | 4/1958 | Wurzburger | 72/367 |
| 2,831,668 | 4/1958 | Skowronski | 51/59 SS |
| 2,855,244 | 10/1958 | Camp | 51/59 SS |
| 3,154,890 | 11/1964 | Lemelson | 51/59 SS |
| 3,368,280 | 2/1968 | Friedman et al. | 32/58 |
| 3,518,766 | 7/1970 | Burt | 32/58 |
| 3,569,748 | 3/1971 | Minchenko et al. | 51/59 SS |
| 3,589,012 | 6/1971 | Richman | 32/58 |
| 3,593,425 | 7/1971 | Robinson | 32/58 |
| 3,654,502 | 4/1972 | Carmona et al. | 32/58 |
| 3,842,632 | 10/1974 | Nelson | 72/367 |
| 3,924,335 | 12/1975 | Balamuth et al. | 32/58 |
| 3,930,173 | 12/1975 | Banko | 32/58 |
| 4,110,908 | 9/1978 | Cranston | 32/58 |

Primary Examiner—Robert Peshock
Assistant Examiner—John J. Wilson
Attorney, Agent, or Firm—Darby & Darby

[57] ABSTRACT

In one embodiment an ultrasonic transducer is provided in which the work tip is formed of a piece of tubular material and a substantial portion, or all, of the tip has a constantly diminishing cross-section approaching the end of the tip. The fluid for the work tip is delivered through the hollow tip to its end. Other embodiments of fluid delivery systems are also disclosed.

2 Claims, 8 Drawing Figures

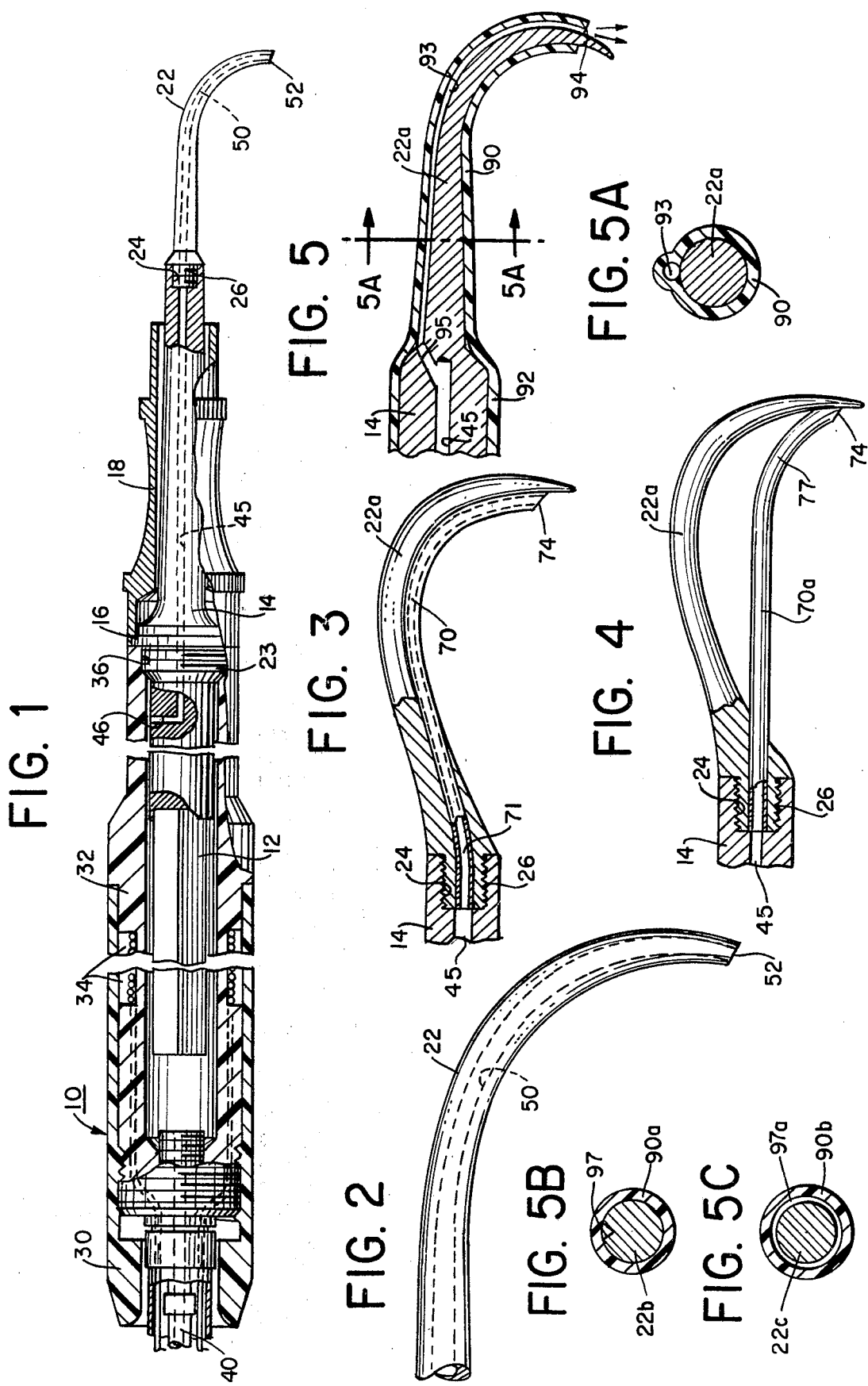

ULTRASONIC TRANSDUCER TIPS

Ultrasonic transducers for various purposes, for example dental use, are well known in the art. Reference is made, for example, to U.S. Pat. Nos. 3,368,280 to Friedman et al and 3,075, 288 to Balamuth et al. In transducers of this type, it is sometimes desirable to supply fluid for cutting, cooling and/or treatment purposes. In some cases, the fluid supplied is the same fluid which is used to cool the transducer.

In both the aforesaid Friedman et al and Balamuth et al patents, an arrangement is used wherein a hole is drilled or otherwise formed through a part of the tip and its shank which is used to connect the tip to the rest of the transducer. Water is expelled from the transducer through the shank and the hole in a stream. In the Richman et al patent the water flows in a stream across a dog leg bend of the tip and impinges on its end.

In each of the foregoing patents, the tip is made of a piece of solid metal material which is machined to the desired shape and through which a fluid passage is drilled or otherwise formed for part of the tip length. While such arrangements are in many cases satisfactory, they are costly from a manufacturing point of view. The reason for this is that the machining for the tip shape and fluid passage requires rather precise work because the tip must be shaped to distribute stresses along its length in a manner so that the tip will not be damaged as it vibrates.

The preferred embodiment of the present invention relates to an ultrasonic transducer and particularly a tip therefor which is made of material which is effectively tubular. In accordance with the invention, the tip has a continuous through passage to its end and also has a diminishing cross-section towards its end. The tip of the present invention can be made fairly inexpensively since relatively little machining is required, with the major portion being done on the outer surface of the tubular material. The machining is carried out in a simple manner which can be accomplished easily, inexpensively and with a high degree of precision. Water is delivered through the hollow portion of the tubular tip.

Other water delivery systems for transducer tips are also disclosed, one being a tube external to the tip and conforming to its shape to deliver water to the end of the tip and a second where a tube bridges a bent tip to deliver water to its end. A third embodiment uses a sleeve external to the tip for delivering fluid to the tip end.

It is therefore an object of the present invention to provide a novel tip for an ultrasonic transducer.

A further object is to provide a tip for an ultrasonic transducer made of tubular material.

An additional object is to provide a tip for an ultrasonic transducer made of tubular material having a diminishing, cross-section throughout its length.

Yet a further object is to provide various types of water delivery systems for the tip of an ultrasonic transducer.

Other objects and advantages of the present invention will become more apparent upon reference to the following specification and annexed drawings in which:

FIG. 1 is a plan view, taken partly in cross-section, of an ultrasonic transducer in accordance with the invention;

FIG. 2 is an enlarged fragmentary view of the tip;

FIGS. 3–5 are fragmentary views of the end of the tip having various types of fluid delivery systems;

FIG. 5A is a cross-section of the sleeve of the embodiment of FIG. 5; and

FIGS. 5B and 5C are cross-sections of further modifications of the embodiment of FIG. 5.

Referring to FIGS. 1 and 2, the ultrasonic transducer 10 comprises the usual stack of laminations 12 of a suitable magnetostrictive material, for example, Monel. The stack 12 is generally one-half wavelength long at the operating frequency of the transducer. A connecting body, or acoustic transformer 14, is attached to an end of the stack 12. The acoustic transformer is preferably tapered so as to provide a good impedance match. In the embodiment of the invention shown, the transducer is of the general type shown in copending application Ser. No. 412,767 to Anton Banko, filed Nov. 5, 1973, now U.S. Pat. No. 3,930,173 which is assigned to the assignee of the subject application.

The connecting body 14 has an integrally attached flange 16 which is located in the approximate vicinity of a node point of the ultrasonic energy as the connecting body 14. A shell 18 is connected to and extends forwardly from the flange. The shell 18 is substantially one-quarter wavelength long at the resonant frequency of the transducer. The outer surface of the connecting body 14 to the left of the flange 16 has threads 23, whose purpose is to be described. A tip 22, which is described in greater detail below, is fastened to the acoustic transformer 14. The connection can be made by welding, brazing or else by a threaded screw. The latter arrangement is shown in which the end of the acoustic impedance transformer 14 has a threaded hole 24 and the inner surface of the tip 22 is threaded at 26.

An outer housing 30 is provided which fits over an inner jacket 32. A coil of wire 34 is wound over a narrowed down position of jacket 32. The coil is covered by housing 30. The coil 34 receives electrical current which reacts with the magnetostrictive stack of magnetostrictive laminations 12 to produce a compressional wave. The compressional wave is conveyed by the transformer 14 to the tip 22. The transformer provides an impedance match between the transformer and the tip.

The right end of jacket 32 has interior threads 36 to mate with the threads 23 on the outside of the transducer body. The end of the jacket 32 abuts against the flange 16 when the jacket is screwed to the body to provide a fluid-tight seal.

A fluid supply line 40 passes through appropriate fittings through the end of the housing 30 into the chamber formed by jacket 30 which surrounds the stack 12. Fluid is supplied through line 40 into the chamber and flows around the stack 12 to cool it. The fluid also flows through a longitudinal passage 45 in the transformer 14. The passage 45 lies along the central axis of the transformer 14 so that it will not adversely affect its energy transfer function. An inlet 46 to passage 45 is formed in transformer 14 generally transverse to the transformer longitudinal axis to communicate with the fluid in the chamber. The elongated passageway 45 also extends to the beginning of the threaded hole 24 to which the tip 22 is attached. Thus, the fluid from supply line 40 can pass through the acoustic transformer to the tip.

FIG. 2 shows further details of the tip 22. The tip has a central channel 50, which is drilled or otherwise formed through the tip. As indicated previously, the tip 22 is preferably made of a piece of pre-formed tubular metal. Therefore, the channel 50 would already be present. Alternatively, a piece of solid material can be used and the channel 50 then drilled or otherwise formed. Channel 50 can be of constant diameter or of diminishing diameter toward the end remote from threads 26. In the latter case, a tubular piece with a minimum desired diameter cross-section for the tip end can be used and then the passage 50 enlarged by a suitable drilling or reaming technique so that the diameter of the channel 50 decreases as it goes toward its end 52. As shown, the passge 50 terminates at the very end 52 of the tip. However, it could be made to terminate short of the end of the tip so that the fluid can be ejected at any desired point. The exit passage for channel 52 can come off at an angle to channel 50 if desired.

As is also shown, the tip 22 is of diminishing cross-section toward its end 52. That is, the tip becomes narrower towards its end. This can be accomplished, as indicated previously, by taking the piece of tubular material and shaping its outer surface by any suitable technique, for example, milling, grinding or swaging. All of these techniques are easy to perform with a high degree of precision.

The tip 22 is shown as having a bend of a gradual arcuate shape. It should be understood that any suitable shape tip can be used. That is, the bend can be on an angle. The tip 22 is preferably bent to the desired shape after its cross-section is established in the manner described above.

The tip end 52 can be left cylindrical or, if desired, it can be flattened. The flattening can be accomplished by hammering or compressing the end of the tip. Care should be taken to avoid constricting the passage.

While in general it is desirable to work with tubular materials for the tip 22 which are generally cylindrical in shape, other shapes can be used. For example, a rectangular tubular member can be used and the sides ground or planed down to achieve the constantly diminishing cross-section. In each case the technique is the same and it generally comprises taking a blank or tubular piece of stock, drilling a hole for channel 50 if the piece is not tubular, and machining the outer surface of piece of stock to achieve the constantly diminishing cross-section.

With respect to the tip, the major portion or all of its length has a continuously diminishing cross-section toward its end 52. The rate of decrease is constant, hyperbolic or some other function consistent with the operation of the transducer. That is, as one goes toward the end 52 of the tip, further from the point of attachment there is less stress. Therefore, a lesser amount of material can be used to accommodate the decreased stress. In an arcuate shaped tip, the decrease in stress toward the tip end follows a hyperbolic type function. Therefore, the decrease in cross-sectional tip area can be hyperbolic.

While a magnetostructure stack 12 has been shown for converting the electrical energy supplied by the coil into the vibrating energy, it should be understood that other equivalent means can be used. For example, a piezoelectric body can be used to perform this function as is conventional in the art. Devices using such piezoelectric bodies also utilize the acoustic impedance transformer and the work tip.

FIG. 3 shows another embodiment of water delivery system for the tip. While the tip of FIGS. 1 and 2 is illustrated, it should be understood that other types of tips can be used. In FIG. 3, a tube 70 is provided having one end 71 inserted into a hole 72 in the threaded tip end 26 to thereby communicate with the fluid passage 45. The end 71 can be welded or otherwise attached in a fluid-tight manner to shank 24. Tube 70 is bent to conform to the inner shape of the tip 22a, which is solid in this case. The tube 70 and tip 22a are attached to each other for example, by welding, brazing, soldering, swaging or any other suitable process. The open end 74 of tube 70 is cut at an angle to deliver the fluid from the passage, and terminates short of the end of the transducer tip 22a to leave it unobstructed for scaling action. Using the arrangement of FIG. 3, the fluid can be directed more or less directly from the end 74 of tube 70 into the mouth or onto the teeth rather than impinging on the end of the tip 22a. The tube end 74 can be formed to provide water both to end of tip 22a and to the teeth. Also, the tube 70 can be bent around the outer curvature of tip 22a rather than the inner curvature, as shown. In this case, the fluid would be directed from the back of the tip rather than the front.

FIG. 4 shows a modification of the embodiment of FIG. 3. Here tube 70a is provided which is substantially straight instead of being bent as shown in FIG. 3. The end 77 of tube 70a is attached, such as by soldering, brazing or welding to tip 22a near its end. Tube end 77 is bent slightly to provide a larger contact area for the attachment. This embodiment has an advantage in that the tube 70a can be substantially straight or bent only slightly. This simplifies manufacture.

In the case of the tubes 70 and 70a of FIGS. 3 and 4, these are preferably made of metal. Non-metallic tubes also can be used.

FIGS. 5 and 5A show a further embodiment wherein the fluid is delivered external to the tip. Here a sleeve 90 is provided around the solid tip 22a. Sleeve 90 can be molded or shaped of a suitable material, for example, silicone rubber, plastic, etc. One end 92 of sleeve 90 is attached to the end of connecting body 14 such as by a force fit, by an adhesive or by a mechanical means such as a clamp (not shown). One or more passages 93 are formed from the outer end of the sleeve to an intermediate point where the fluid is to be supplied to it from the channel 45. Passage 93 is shown as being generally circular. However, it can be flat and wide. The passage(s) 93 communicates with an opening 95 in the end of connecting body to communicate with the channel 45. Passage 93 has an end opening 94 through which the water exits. Thus, water is directed to the passage 93 from channel 45 and out the passage opening 94 onto the teeth or into the mouth.

One preferred way of forming sleeve 90 is to mold it directly over and onto the outer surface of tip 22. The passage(s) 93 is also formed during the molding operation. This can be done, for example, by setting a wire or other member in place where the passage is to exist and then withdrawing the wire to form the passage during or after the molding.

The passage 93 is shown bending around the outer curve of tip 22a. It can also conform to the inner curved shape of the tip, the side, or any combination thereof. Where two or more passages are used the sleeve 90 can have a manifold passage which communicates with the opening 95 in the connecting body. The passages can be of different diameters, or widths, and have different exit angles to provide for different water volumes, sprays, velocities and/or direction. Also, the opening 94 can be at an intermediate point on the sleeve. For example, the passage 93 can be on the inner radius of a curved tip and the fluid ejected from passage 93 at a point along the radius short of the end of the sleeve.

FIG. 5B shows the cross-section of a further embodiment in which a sleeve 90a is used which fits around the solid tip 22a. The sleeve 90a has no passages. However, the tip 22a has an elongated groove 97 to provide a fluid flow passage. That is, the fluid would travel in the groove of the tip confined by the sleeve 90a and would exit where the sleeve ended. The groove 97 can be on the outer or inner curvature of the tip or on a side. There can be only one groove 97 or a multiplicity of such grooves on the tip. In the latter case, a manifold groove (not shown) would be provided to communicate with the fluid exit passage 95 and with the various grooves. The grooves can be provided on the inner and/or outer curvatures and/or sides. They can be curved or flat.

In the embodiment of FIG. 5C, the end 92 of the sleeve (not shown) is attached as in FIG. 5. However, here there is a clearance around the entire circumference of the sleeve so that water will exit from the sleeve front end all around the end of the tip 22a. If desired, a spring can be obtained by providing small blockages at the exit end of the sleeve.

What is claimed is:

1. An ultrasonic transducer comprising means for converting electrical energy into vibratory energy, acoustic impedance transformer means coupled to one end of said converting means, and a work tip having one end coupled to the other end of said acoustic impedance transformer means and a free end which vibrates upon receiving the vibratory energy from said converting means through said transformer means, means for supplying fluid to said transducer, and means for delivering fluid from said supplying means to be discharged from an area of said tip, said delivering means comprising a sleeve conforming to the shape of and closely fully surrounding said tip along a substantial portion of its length, and at least one groove formed in said work tip receiving fluid from said supplying means and forming a passage between said sleeve and said tip through which the fluid is discharged, the fluid being in contact with said tip along the length of said passage.

2. An ultrasonic transducer comprising means for converting electrical energy into vibratory energy, acoustic impedance transformer means coupled to one end of said converting means, and a work tip having one end coupled to the other end of said acoustic impedance transformer means and a free end which vibrates upon receiving the vibratory energy from said converting means through said transformer means, means for supplying fluid to said transducer, and means for delivering fluid from said supplying means to be discharged from an area of said tip, said delivering means comprising a sleeve conforming to the shape of and closely fully surrounding said tip along a substantial portion of its length and being spaced from said work tip about its entire outer periphery forming a passage between said sleeve and said tip through which the fluid is discharged, the fluid being in contact with said tip along the length of said passage.

* * * * *